United States Patent [19]

Peuker

[11] Patent Number: 4,484,823
[45] Date of Patent: * Nov. 27, 1984

[54] METHOD OF DETERMINING THE BOILING POINT OF A LIQUID

[75] Inventor: Karl Peuker, Ebern, Fed. Rep. of Germany

[73] Assignee: FAG Kugelfischer Georg Schäfer & Co., Schweinfurt, Fed. Rep. of Germany

[*] Notice: The portion of the term of this patent subsequent to Oct. 11, 2000 has been disclaimed.

[21] Appl. No.: 416,132

[22] Filed: Sep. 9, 1982

Related U.S. Application Data

[63] Continuation-in-part of Ser. No. 339,104, Jan. 13, 1982, Pat. No. 4,408,902.

[30] Foreign Application Priority Data

Jan. 17, 1981 [EP] European Pat. Off. ........ 81100334.2
Sep. 10, 1981 [EP] European Pat. Off. ........ 81107111.7

[51] Int. Cl.$^3$ ............................................. G01N 25/08
[52] U.S. Cl. ...................................... 374/27; 73/61.3; 374/54
[58] Field of Search .................. 374/27, 25, 16, 24, 374/11, 20; 73/61.3; 338/14

[56] References Cited

U.S. PATENT DOCUMENTS

| | | | |
|---|---|---|---|
| 3,447,358 | 6/1969 | Crespin et al. | 374/16 |
| 3,675,465 | 7/1972 | Sommer et al. | 374/11 |
| 4,059,982 | 11/1977 | Peuker | 374/27 |
| 4,413,170 | 11/1983 | Val et al. | 219/505 X |

FOREIGN PATENT DOCUMENTS 2721232 11/1978 Fed. Rep. of Germany ........ 374/27

*Primary Examiner*—Daniel M. Yasich
*Attorney, Agent, or Firm*—Karl F. Ross; Herbert Dubno

[57] ABSTRACT

In order to determine the boiling point of a liquid, especially a nonaqueous one such as a brake fluid, a device suspended in a body of that liquid—e.g. in a reservoir supplying fluid to a brake cylinder—forms a narrow chamber which is open at the bottom and the top and which contains means for heating the liquid in that chamber and measuring its temperature; the two functions can be simultaneously performed by a thermistor. When the boiling point is reached and the liquid in the chamber is vaporized, partial evaporation of that liquid and replacement thereof by fresh liquid from the main body results in a leveling of the temperature curve; the boiling point marked by this event can be read on a meter and/or qualitatively indicated by differently colored lights, for example. An excessive temperature rise early in the test will also show an unduly low liquid level in the reservoir.

3 Claims, 4 Drawing Figures

METHOD OF DETERMINING THE BOILING POINT OF A LIQUID

CROSS-REFERENCE TO RELATED APPLICATION

This is a continuation-in-part of my copending application Ser. No. 339,104 filed Jan. 13, 1982 now U.S. Pat. No. 4,408,902.

FIELD OF THE INVENTION

My present invention relates to a method of determining the boiling point of a liquid, especially a nonaqueous one such as the brake fluid of an automotive vehicle.

BACKGROUND OF THE INVENTION

A known device for testing a brake fluid and detecting its boiling point comprises a heating cup into which some of the fluid is injected with the aid of a syringe. After being closed against the atmosphere, the cup is heated until evolving gas bubbles begin to pass through a U-shaped tube into a receptacle therefor. The temperature at which this occurs is noted as the boiling point, whereupon the liquid in the cup is returned to the brake system of the vehicle by means of the same syringe; both the cup and the syringe are then carefully cleansed preparatorily to a new test. Such a device is relatively expensive and cumbersome to handle, being thus not very well suited for use in a repair shop for automotive vehicles.

In my above-identified copending application and patent I have disclosed a method of boiling-point determination according to which a quantity of the liquid to be tested is confined in a narrow boiling chamber that is closed at the top and is in communication at its bottom with a larger body of the same liquid. During gradual heating of the liquid so confined, the temperature in the space is continuously measured. When that liquid begins to boil, the rate of temperature rise undergoes a significant change; thus, if the temperature is measured near the top of a narrow test space from which the liquid is quickly displaced by evolving vapors, the heat generated in the vicinity of the sensor used for the temperature measurement is less rapidly conducted to the larger body of liquid so that the rate of temperature rise undergoes a steep increase. Such a rate change is taken as an indication that the boiling point has been reached.

While the system described in my prior U.S. Pat. No. 4,408,902 operates satisfactorily, it requires the use of two separate instruments to measure the actual temperature as well as the temperature rise. Another inconvenience is the need for sealing the boiling chamber against the atmosphere during a test.

OBJECT OF THE INVENTION

The object of my present invention, therefore, is to provide an improved method of boiling-point determination which obviates these drawbacks.

SUMMARY OF THE INVENTION

I have found, in accordance with the present improvement, that a clear indication of the boiling point can be obtained when the space containing the liquid to be heated, namely the aforementioned boiling chamber, is open at its top to a larger gas volume (possibly to the ambient atmosphere) instead of being closed as in the method of my prior patent. As the bottom of the boiling chamber opens onto a larger body of the same liquid, the part vaporizing in the chamber upon attainment of the boiling point escapes through the open top and is instantly replaced by fresh liquid from below which mingles with the hot liquid in that chamber and assumes its temperature. Thus, the output signal of a heat sensor levels off as soon as the boiling point is reached; that point, therefore, can be conveniently read on the scale of a meter whose indicator has become stationary.

As described in my prior U.S. Pat. No. 4,408,902, a temperature sensor and a heater may be separately immersed into the liquid but could also be combined into a single unit such as, for example, a positive thermistor. The heating and sensing means, of course, must be covered by enough liquid to prevent their exposure to a gas space as the liquid level progressively drops during a test; this drop will be insignificant if the volumetric ratio between the surrounding liquid body and the contents of the boiling chamber is large.

If for any reason the boiling chamber is insufficiently filled with liquid at the beginning of the heating operation, a steep temperature rise will occur early in the test. Thus, a comparison of the initial rate of temperature increase with a reference value may be used for ascertaining a possible absence of liquid in that space.

The present method can be implemented by a device similar to that disclosed in my aforementioned patent, comprising a probe suspended in a container for the liquid to be tested. According to that patent, a heat-insulated chamber is closable at its top against the atmosphere while communicating at its bottom with the interior of the container below whose normal liquid level the chamber is located; with the modified method the chamber top is left open to a relatively large gas volume in the surrounding container or directly to the atmosphere. The chamber contains heating and temperature-measuring means connected to external display means for signaling the aforementioned rate change, namely the leveling of the temperature curve, as an indication that the boiling point of the liquid has been reached. Again, the heating and temperature-measuring means may be combined into a single unit, specifically a thermistor connected across a source of substantially constant voltage. The current drawn by the thermistor will heat the liquid and will also serve as a temperature-indicating parameter.

BRIEF DESCRIPTION OF THE DRAWING

The above and other features of my invention will now be described in detail with reference to the accompanying drawing in which.

SPECIFIC DESCRIPTION

Figure 1:
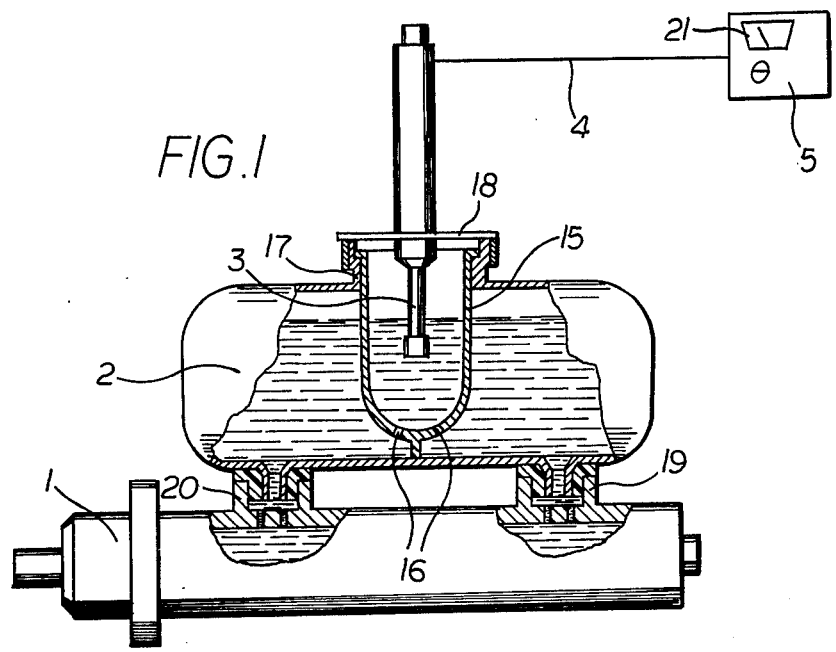
FIG. 1 is a somewhat diagrammatic, partly sectional side-elevational view of a device embodying my invention.
Figure 3:
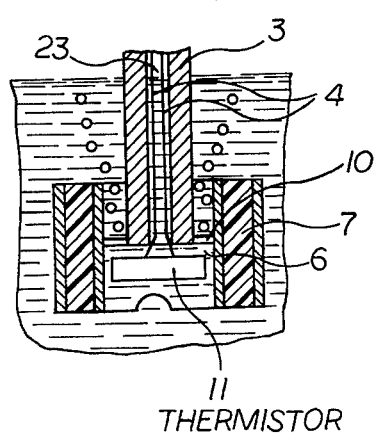
FIGS. 3 and 4 are sectional detail views, drawn to a larger scale, of a probe forming part of the device of FIG. 1.
Figure 4:
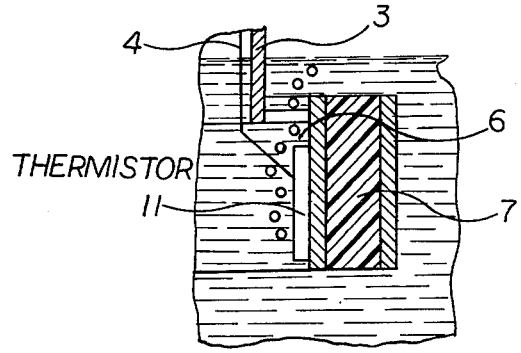

In FIG. 1 I have shown a vessel 1, e.g. the main cylinder of an automotive brake system, supplied with brake fluid from an overlying reservoir 2 by way of tubular supports 19 and 20. A container 15 with bottom openings 16, immersed in the liquid, is supported by a flange 17 formed at the top of that reservoir. A probe 3, more fully described hereinafter with reference to FIGS. 3 and 4, is rigid with a lid 18 and is suspended inside container 15 when that lid comes to rest upon flange 17. Probe 3 forms a downwardly open chamber 6 which lies below the liquid level in reservoir 2.

As shown is FIG. 3, the preferably cylindrical chamber 6 has a heat-insulated peripheral wall 7 of plastic material which may be internally and externally coated with a protective layer. The top of first chamber 6 communicates with a second chamber inside container 15 through an annular space surrounding the stem of probe 3 to which the chamber 6 is fastened by spokes 10. Air escapes from the chamber 6 through a gap between flange 17 and lid 18 when the probe is slowly lowered into the container 15 so that the surrounding liquid enters the chamber through its open bottom. Chamber 6 is also vented to the atmosphere through an axial bore 23 of the stem.

FIG. 3 further shows a combined heater and temperature sensor in the form of a thermistor 11 disposed in the chamber 6 so as to be surrounded with small clearance by its wall 7. Thermistor 11 is connected by a cable 4, received in bore 23, to a display panel 5 provided with a temperature indicator 21 which may be a simple milliammeter with a suitably graduated scale.

Figure 2:
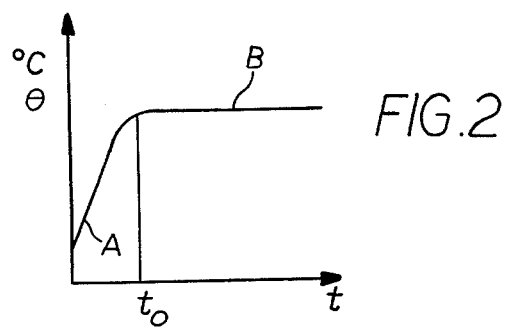
FIG. 2 is a graph showing temperature as a function of time in the practice of my present method.

When the thermistor 11 is energized, the temperature $\theta$ indicated by meter 21 will rise gradually and substantially linearly as indicated at A in FIG. 2. When the boiling point of the liquid is reached, i.e. at a time $t_o$, the liquid in the vicinity of the thermistor quickly evaporates and forms gas bubbles rising into the air space of container 15 while fresh, colder liquid from the lower part of the container takes its place within chamber 6 where it is promptly heated up to a temperature near the boiling point. This results in a leveling of the temperature curve as represented by a line B in FIG. 2 and as visualized by meter 21; the operator, on noting that the pointer of that indicator has stopped advancing, reads the temperature value indicated by that pointer.

As shown in FIG. 4, the thermistor 11 may be positioned close to the inner surface of chamber wall 7, i.e. directly under the annular gap which opens into the vessel 15 of FIG. 1. Naturally, the illustrated thermistor may be one of several such devices disposed at peripherally spaced locations and energized in parallel or in series by way of cable 4.

The display panel 5 of FIG. 1 may be replaced by a different indicator, as disclosed in my prior patent identified above, whose electronic circuitry includes several threshold comparators energizing respective light sources if the boiling point is found to lie above, at, or below the critical value. Thus, for example, one light-emitting diode may glow red when the boiling point lies in an "unsatisfactory" range below the critical level, the light of another such diode indicating by a yellow color a "barely acceptable" value close to that critical level, whereas green light from a third diode may show a "safe" range well above that level.

For convenience, the visual indicator 5 or its equivalent may be mounted directly on the lid 18 of probe 3. While that lid is not essential in the present instance, it retards the evaporation of the test liquid from container 15.

EXAMPLE

A directly heated thermistor of positive resistance/temperature characteristic, designed as a heating coil occupying an area of 4×4 mm, was immersed in 20 cm$^3$ of brake fluid and energized with 14 volts, its resistance at room temperature being 15 ohms. Gas bubbles began to evolve along the heating coil after 10 seconds while a meter in series with the thermistor stopped after rising to the boiling point of the liquid.

The described probe could be installed at any suitable location of an automotive vehicle, e.g. in the vicinity of a brake or wheel cylinder or in a conduit carrying the brake fluid. At these locations the boiling point is usually several degrees lower than in a storage tank.

I claim:

1. A method of determining the boiling point of a liquid, comprising the steps of:
    (a) confining a quantity of the liquid to be tested in a first chamber in a container having a space open at the top to a larger gas volume and in communication at the bottom with a larger body of the same liquid;
    (b) gradually heating the liquid in said space with a sensor in a probe;
    (c) continuously measuring the temperature by said probe in a space in a second chamber within said probe during the heating step; and
    (d) registering the occurrence of a substantial cessation of temperature rise measured in step (c) as an indication of the boiling point of the liquid having been reached.

2. A method as defined in claim 1, comprising the further step of comparing an initial rate of temperature rise with a reference value for ascertaining a possible absence of liquid in said space in said second chamber.

3. A method as defined in claim 1 or 2 wherein the heating in step (b) and the measuring of temperature in step (c) are performed by energizing a thermistor immersed in the liquid in said second chamber and measuring the energizing current drawn by said thermistor.

* * * * *